United States Patent
Atkinson et al.

(10) Patent No.: US 9,687,235 B2
(45) Date of Patent: Jun. 27, 2017

(54) DOUBLE-ROW RATCHET LOCKING MECHANISM WITH SINGLE-BYPASS ('ARMING') FUNCTIONALITY

(71) Applicant: INNOVATIVE TRAUMA CARE, INC., Edmonton (CA)

(72) Inventors: Ian Atkinson, Cochrane (CA); Dennis Filips, Ottawa (CA); Prasanna Lakshminarasimhan, Edmonton (CA); Steve Dralle, San Antonio, TX (US); Kelly Mottet, Edmonton (CA); Chuck Luddy, Alexandria, VA (US); Kathleen McHugh, Alexandria, VA (US); Christian Leon Haller, Alexandria, VA (US)

(73) Assignee: Innovative Trauma Care, Inc., Edmonton (CA)

( * ) Notice: Subject to any disclaimer, the term of this patent is extended or adjusted under 35 U.S.C. 154(b) by 136 days.

(21) Appl. No.: 14/567,842

(22) Filed: Dec. 11, 2014

(65) Prior Publication Data
US 2015/0164504 A1  Jun. 18, 2015

Related U.S. Application Data

(60) Provisional application No. 61/914,901, filed on Dec. 11, 2013.

(51) Int. Cl.
| A61B 17/08 | (2006.01) |
| A61D 1/00 | (2006.01) |
| A61B 17/00 | (2006.01) |

(52) U.S. Cl.
CPC ............ *A61B 17/08* (2013.01); *A61B 17/083* (2013.01); *A61B 2017/00407* (2013.01);
(Continued)

(58) Field of Classification Search
CPC . A61B 17/08; A61B 17/083; A61B 2017/081; A61B 17/064;
(Continued)

(56) References Cited

U.S. PATENT DOCUMENTS

| 4,341,100 A | 7/1982 | Kohlhage |
| 4,441,528 A | 4/1984 | Julich |

(Continued)

FOREIGN PATENT DOCUMENTS

WO   WO 2012/051706 A1   4/2012

OTHER PUBLICATIONS

Holley, J.: "*How the iTClamp Works, Putting the Clamp on Hemorrhage*" [online], Copyright 2013 PeanWell Corporation. A supplement to JEMS Dec. 2013. [retrieved on Jun. 12, 2015]. Retrieved from the internet: <URL:http:Thes-emergencias.com/wp content/uploads/2013/12/ITraumaSupp_Dec20  I  3JEMS_medres_lowpd15.

International Search Report issued on Jun. 22, 2015 regarding PCT/IB2014/003154.

*Primary Examiner* — Katherine M Shi
(74) *Attorney, Agent, or Firm* — DLA Piper LLP (US)

(57) ABSTRACT

The present disclosure provides a wound closure device including: (a) a first opposing member and a second opposing member disposed on opposing sides of a central axis, each resiliently moveable between a closed position and open position relative to each other, each of the opposing members having a distal edge; (b) skin penetrating means for anchoring the device; (c) a pressure bar along each distal edge; (d) releasable locking means for biasing or maintaining the device in the closed position; and optionally (e) an accessory component.

40 Claims, 13 Drawing Sheets

(52) U.S. Cl.
CPC ... *A61B 2017/081* (2013.01); *A61B 2017/088* (2013.01); *Y10T 74/2133* (2015.01)

(58) Field of Classification Search
CPC ............ A61B 2017/2837; A61B 90/57; A61M 2025/024; A61M 2025/0286; A61M 25/02; B25B 13/463; B25B 13/467; B25B 17/00; Y10T 74/2133
USPC ....... 606/218, 221; 192/48.92, 48.3; 74/575; 70/337, DIG. 63
See application file for complete search history.

(56) References Cited

U.S. PATENT DOCUMENTS

| | | |
|---|---|---|
| 4,475,420 A | 10/1984 | Atkinson et al. |
| 4,852,618 A | 8/1989 | Zollinger et al. |
| 5,172,294 A | 12/1992 | Ineichin et al. |
| 5,301,824 A | 4/1994 | Schoeller |
| 5,417,684 A | 5/1995 | Jackson et al. |
| 5,486,196 A | 1/1996 | Hirshowitz et al. |
| 5,827,323 A | 10/1998 | Klieman et al. |
| 6,339,977 B1 * | 1/2002 | Lee ................... B25B 13/466 192/43 |
| 7,070,058 B2 | 7/2006 | Strobel |
| 7,235,090 B2 | 6/2007 | Buckman et al. |
| 7,416,254 B2 | 8/2008 | Jennings |
| 8,496,668 B2 | 7/2013 | Rice et al. |
| 8,561,772 B2 | 10/2013 | Papania et al. |

* cited by examiner

DOUBLE-ROW RATCHET LOCKING MECHANISM WITH SINGLE-BYPASS ('ARMING') FUNCTIONALITY

CROSS REFERENCE TO RELATED APPLICATION(S)

This application claims the benefit under 35 USC §119(e) to U.S. Application Ser. No. 61/914,901 filed Dec. 11, 2013, the disclosure of which is considered part of and is incorporated by reference in the disclosure of this application.

FIELD OF THE INVENTION

The present invention relates to a mechanical locking mechanism. In particular, the invention relates to a one-way locking mechanism that utilizes a double-row ratchet.

BACKGROUND

The rapid control of severe bleeding at wound sites is of critical importance in wound management, especially for the management of trauma or surgery. During certain types of wound injury in high-stress austere environments, such as a dissected artery on the battlefield, the access hole of shrapnel or a bullet must be closed rapidly to avoid excess blood loss.

The gold standard is the use of sutures, staples, adhesives, cautery or fibrin sealants by surgical personnel to stop the flow of blood and close the wound. Appropriate in a hospital setting, the disadvantage of these closure methods in a field setting, especially for care under fire, is that they take a significant length of time to apply and are required to be performed by an expert.

Several approaches to date have been used to close injured wounds in a field setting. The most common approach is to provide manual pressure over the puncture site to compress the damaged blood vessel until the blood coagulates. This is quite difficult not only because of the high blood flow from an artery, but also because there may be many layers of tissue or fabric that have to be compressed by hand or by strap to staunch blood flow from the site of the injury. Manual pressure is considered passive, because of an inability to initiate or accelerate blood clotting. This inefficiency increases the risk of exsanguination as well as reduces the patient's ability to continue to participate in the action and ambulate to a safer location as it may loosen the clot and increase blood loss.

In another approach to close a vessel puncture site, a tourniquet is attached to the patient's extremity proximal to the injury site. The tourniquet applies pressure and collapses the vessel prior to the injury site, reducing blood loss from the opening. The patient, however, must still remove the tourniquet in a timely manner or risk tissue necrosis that may cause loss of the limb or fatal toxicity. Tourniquets are slow and difficult to maneuver and place around the extremity and require fine motor skills. There are also problems associated with the use of tourniquets due to improper forces exerted by these devices which can cause unwanted blood loss as high pressure arterial blood can move beyond the tourniquet, but lower pressure venous blood is unable to pass, actually causing blood loss.

The use of gauzes, felts, sponges, pads and knitted fabrics as field wound dressing combined with manual pressure or pressure dressings is quite conventional. While utilization of bandage and strap assemblies have been widely accepted for field care, these devices present a number of disadvantages. Strap mechanisms of band assemblies are often relatively structurally complex and are difficult to precisely apply about the chest and junctions (armpit, groin, base of the neck). With this approach, it can take a long time to seal the injured artery or vessel and for the patient to be able to ambulate.

To avoid the foregoing disadvantages of manual pressure approaches, impregnated bandages with clotting agents have been developed to introduce clotting factors percutaneously that speed clotting. One such bandage device, referred to as QuickClot™ and sold by Z-Medica, introduces zeolites to the injured vessel, causing water absorption from the blood to the zeolite to concentrate clotting factors and speed up clot formation. However, the bandage device is still subject to movement during extraction of the wounded patient, which can loosen the clot and cause leakage through the puncture site to increase blood loss. In general, the desirable aspects of hemostats are recognized, but new and improved means of controlling blood loss are in demand.

It would therefore be advantageous to provide a device that would more quickly and effectively close openings (punctures) in the skin to reduce blood loss or for wound closure. The iTClamp™ is such a device, as it would advantageously avoid the aforementioned time of applying manual pressure to the opening, simplify the steps required to close the opening, and more effectively retain the closure device on the wound. In addition, the iTClamp™ device increases the patient's ability to continue to participate in the action and ambulate to a safer location. However, the iTClamp™, as well as other similar clamping devices may be improved by providing mechanical means that allow for better resolution of control in clamping.

SUMMARY OF THE INVENTION

The present invention relates to a one-way mechanism that may be utilized as part of a product, such as a clamp device for wound closure. The mechanism is a ratcheting mechanism which includes two concentric disks of engaging sloped teeth that allow for relative rotation of the two disks in only a single direction. One of the disks includes two concentric circles of ratchet teeth, spaced at 2× the desired final rotational pitch (P) of the mechanism and staggered by 1× the final pitch (P) relative to each other. This provides a means to have larger features of size (teeth) to meet manufacturing limitations for a given final pitch (P). A cam feature allows the implementation of a one-time bypass operation of the mechanism ("arming") that is set by two angular positions of the disks relative to each other.

A wound clamp device utilizing the ratchet mechanism rapidly re-approximates the skin edges by engaging the skin to seal the wound. The device is configured to open and close in a clam-shell configuration, and may be configured to be operated one-handed. In one embodiment, the device comprises needles which puncture the skin edges when the device is closed, and a pressure bar which applies pressure substantially perpendicular to the long axis of the wound. In one embodiment, the pressure bar comprises end closure members which are disposed substantially perpendicular to the pressure bar. The pressure is initially exerted manually by closing the device onto the skin surrounding the wound. The device may be maintained in a closed position by a biasing means, by the ratcheting mechanism of the present invention.

Therefore, in one aspect, the invention provides a ratchet mechanism. The mechanism may include: (a) a first opposing disk and second opposing disk rotationally engagable about a longitudinal axis and being rotationally movable about the axis between an open position and a closed position, each disk having a plurality of engaging members disposed on opposing surfaces of each disk such that movement of the mechanism from the open position to the closed position causes opposing rotational movement of each disk relative to one another, wherein the engaging members maintain the opposing disks in the closed position upon movement of the ratchet from the open position to the closed position; (b) a shaft having a first end and a second end, the shaft extending from the second disk along the longitudinal axis toward the first disk from the first end to the second end; and (c) a resilient member arranged along the longitudinal axis between the first disk and the second end of the shaft, wherein application of force to the first end of the shaft along the longitudinal axis disengages the plurality of engaging members allowing opposing rotational movement of the disks from the closed position to the open position. In an embodiment, the plurality of engaging members are arranged as teeth radially disposed around each opposing surface of the first and second disk, and the engaging members of one of the first or second disk are arranged as concentric outer and inner circles, each circle being radially offset to the other.

In another aspect, the invention provides a wound closure device which includes the ratchet mechanism of the present invention. The wound closure device includes (a) a first opposing member and a second opposing member engaged about a longitudinal axis, each pivotally moveable around the axis between a closed position and an open position relative to each other, each of the opposing members having a proximal edge adjacent the longitudinal axis and a distal edge, and an outer face and an inner face; (b) at least one ratchet mechanism of the invention, wherein the first disk is on the first member, and the second disk is on the second member; and (c) a plurality of needles disposed on the distal edges of the first and second members.

In yet another aspect, the invention provides a wound closure device which includes the ratchet mechanism of the present invention which includes: (a) a first opposing member and a second opposing member engaged about a longitudinal axis, each pivotally moveable around the axis between a closed position and an open position relative to each other, each of the opposing members having a proximal edge adjacent the longitudinal axis and a distal edge; (b) skin penetrating means for anchoring the device; (c) a pressure bar along each distal edge; and (d) at least one ratchet mechanism of the invention.

In another aspect, the invention provides a method for performing a medical procedure on a subject using a wound closure device. The method includes (a) deploying the wound closure device of the invention to a wound of the subject; and (b) actuating the wound clamp device to effectuate approximation of skin tissue and closing of the wound closure device.

BRIEF DESCRIPTION OF THE FIGURES

In the drawings, like elements are assigned like reference numerals. The drawings are not necessarily to scale, with the emphasis instead placed upon the principles of the present invention. Additionally, each of the embodiments depicted are but one of a number of possible arrangements utilizing the fundamental concepts of the present invention. The drawings are briefly described as follows.

DETAILED DESCRIPTION

Figure 1:
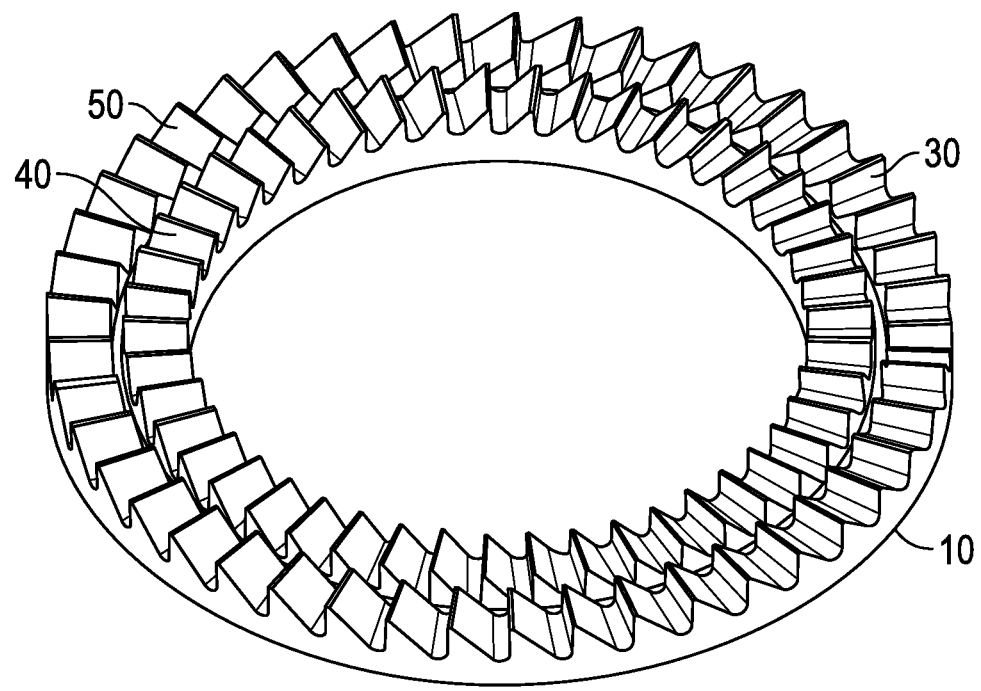
FIG. 1 is an isometric view of disk 10 in one embodiment of a ratchet mechanism.
Figure 2:
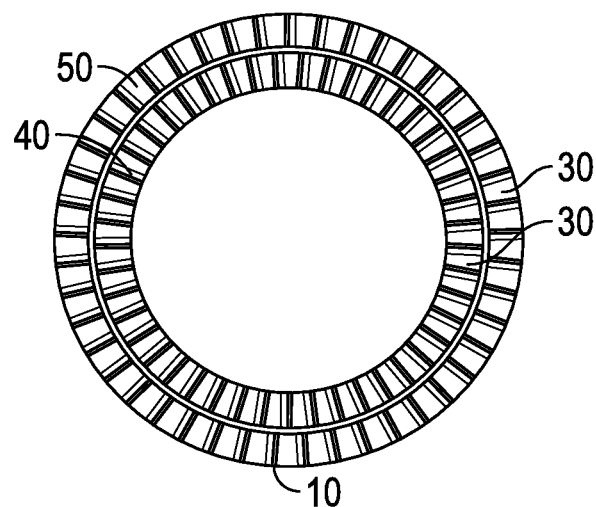
FIG. 2 is a top view of disk 10 in one embodiment of a ratchet mechanism.

The invention relates to a mechanical locking mechanism, specifically, a one-way locking mechanism that utilizes a double-row ratchet. When describing the present invention, all terms not defined herein have their common art-recognized meanings. To the extent that the following description is of a specific embodiment or a particular use of the invention, it is intended to be illustrative only, and not limiting of the claimed invention. The following description is intended to cover all alternatives, modifications and equivalents that are included in the spirit and scope of the invention, as defined in the appended claims.

In general terms, the present disclosure describes an arming and locking mechanism which allows for better resolution of control of clamping devices. A step ratchet mechanism is described that allows for the incremental closure and locking of the arms of a wound closure clamp relative to an axis with a pivot point. The step ratchet mechanism is comprised of a single ratchet on one face, and a double ratchet on the opposing face to increase the number of steps by 2× to increase the resolution of closure. The step ratchet mechanism is actuated by the application of pressure to the arms. This permits small incremental movement along the arc of closure in the closing direction, as the device is squeezed shut with manual digital pressure, causing the ratchet disks to rotate opposite one another about a longitudinal axis. The arms move from a more open to a more closed position, the ratchet rotates without relaxation to the original position based on the orientation of the ratchet teeth. The device arms when squeezed with digital pressure close until the skin provides enough resistance to limit further arm closure movement. The ratchet remains closed and locked in the final position without further involvement, to both secure the arms in the closed position and to keep the pressure bars creating a fluid-tight or air-tight seal of the skin. The arms are maintained in that position by the ratchet until the ratchet faces are separated, rotated one relative to the other, and the arms can then be moved separate and access to the wound is possible.

In one embodiment, the mechanism includes: (a) a first opposing disk and second opposing disk rotationally engagable about a longitudinal axis and being rotationally movable about the axis between an open position and a closed position, each disk having a plurality of engaging members disposed on opposing surfaces of each disk such that movement of the mechanism from the open position to the closed position causes opposing rotational movement of each disk relative to one another, wherein the engaging members maintain the opposing disks in the closed position upon movement of the ratchet from the open position to the closed position; (b) a shaft having a first end and a second end, the shaft extending from the second disk along the longitudinal axis toward the first disk from the first end to the second end; and (c) a resilient member arranged along the longitudinal axis between the first disk and the second end of the shaft, wherein application of force to the first end of the shaft along the longitudinal axis disengages the plurality of engaging members allowing opposing rotational movement of the disks from the closed position to the open position. In an embodiment, the plurality of engaging members are arranged as teeth radially disposed around each opposing surface of the first and second disk, and the engaging members of one of the first or second disk are arranged as concentric outer and inner circles, each circle being radially offset to the other.

Figure 3:
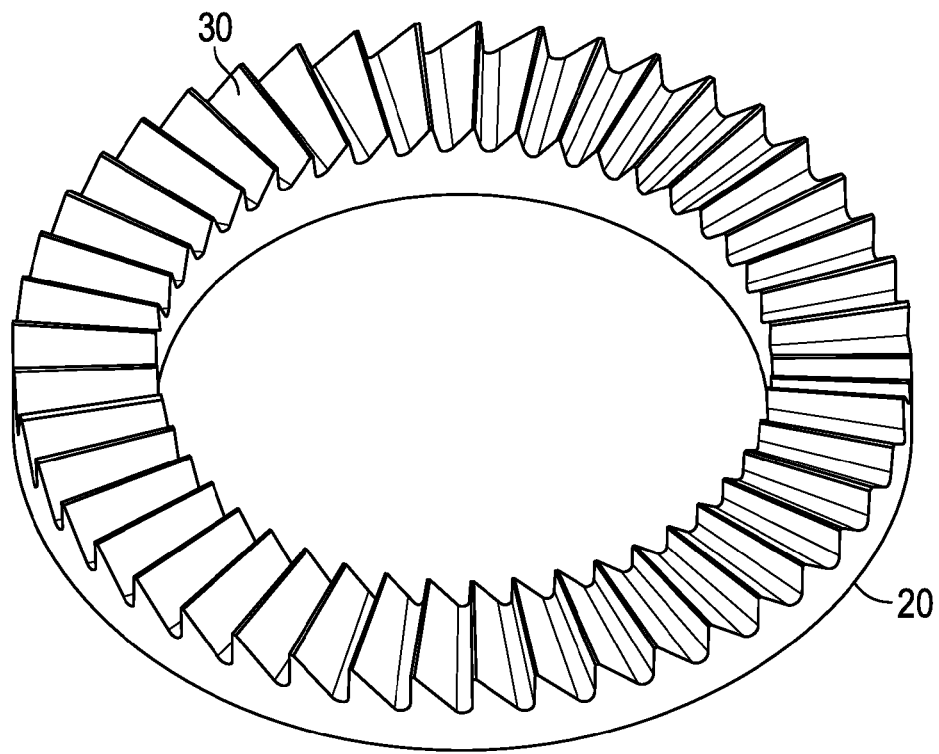
FIG. 3 is an isometric view of disk 20 in one embodiment of a ratchet mechanism.
Figure 4:
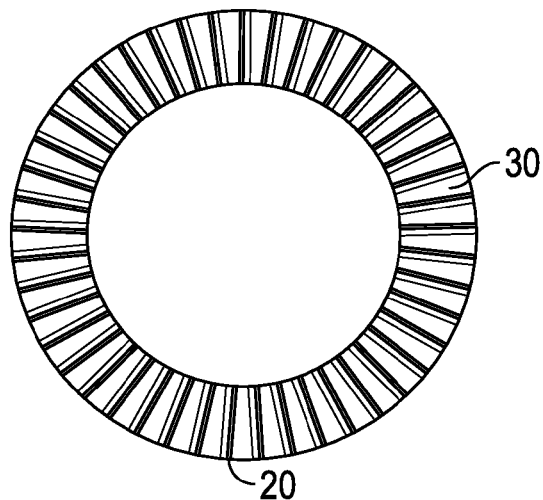
FIG. 4 is a top view of disk 20 in one embodiment of a ratchet mechanism.

With reference to FIGS. 1-5, the ratcheting mechanism includes two opposing disks (10, 20) having of engaging members (30) on opposing surfaces, such as sloped teeth that allow for relative rotation of the two disks in only a single direction while the engaging members are engaged. First disk 10 includes two concentric circles (40, 50) of engaging members (30), i.e., ratchet teeth, spaced at 2× the desired final rotational pitch (P) of the mechanism and staggered by 1× the final pitch (P) relative to each other. Second disk 20 includes a single circle of engaging members (30), i.e., ratchet teeth, spaced at 2× the desired final rotational pitch (P) of the mechanism. In one embodiment, the maximum and minimum radius of disk 20 engaging members are the maximum radius of the outer most circle (50) of engaging members and the minimum radius of the inner most circle (40) of engaging members of disk 10, respectively (FIGS. 3 and 4).

Figure 5:
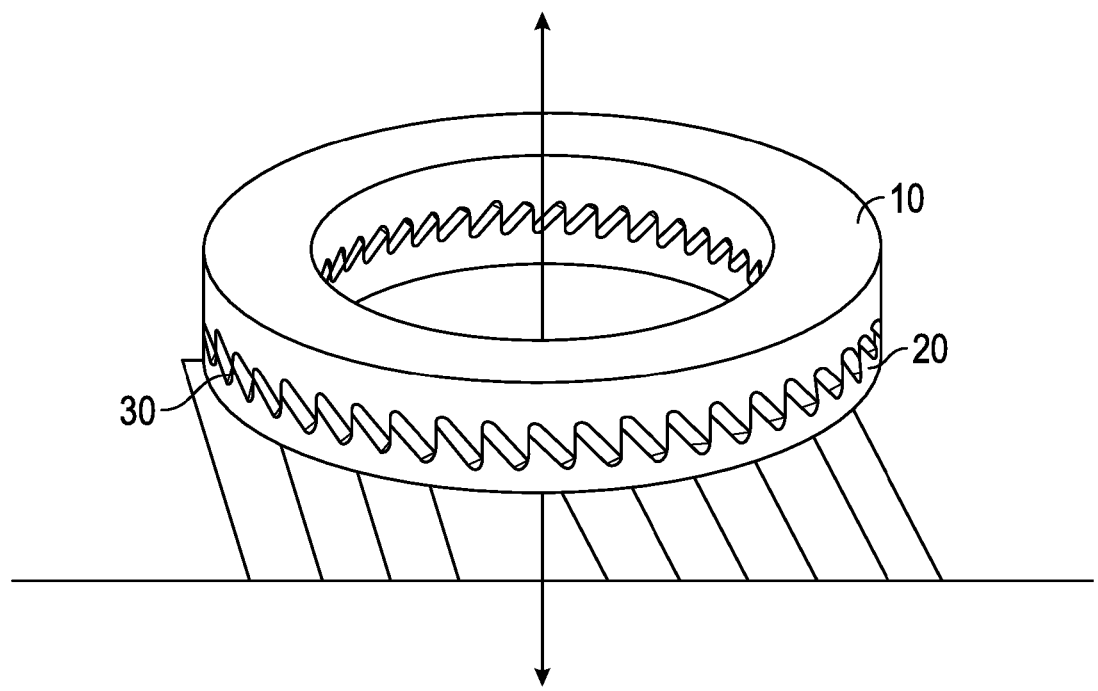
FIG. 5 is an isometric view illustrating interaction of disk 10 and disk 20 in one embodiment of a ratchet mechanism.

While the Figures depict engaging members (30) as sloped teeth, one in the art would understand that the engaging members may have other equivalent geometries. The sloped teeth (30) of disk 10 and 20 engage such that one circle of teeth on disk 10 is positioned to slide up the tooth slope of disk 20 when rotation is in the desired direction of motion. The other circle is positioned against the flat of disk 20 resisting motion in the undesired rotational direction. As the ratchet mechanism rotates in the desired direction the circles of teeth (40, 50) on disk 10 alternate between riding up the slope of disk 20 and resisting motion against the flat of disk 20. The resulting mechanism may have a final pitch of P (FIG. 5). Advantageously, a ratcheting mechanism incorporating a double row ratchet configuration that allows for the pitch between teeth on both disks (10, 20) to be 2× the desired final pitch (P), provides a means to have larger features of size (teeth) to meet manufacturing limitations for a given final pitch (P).

Figure 6:
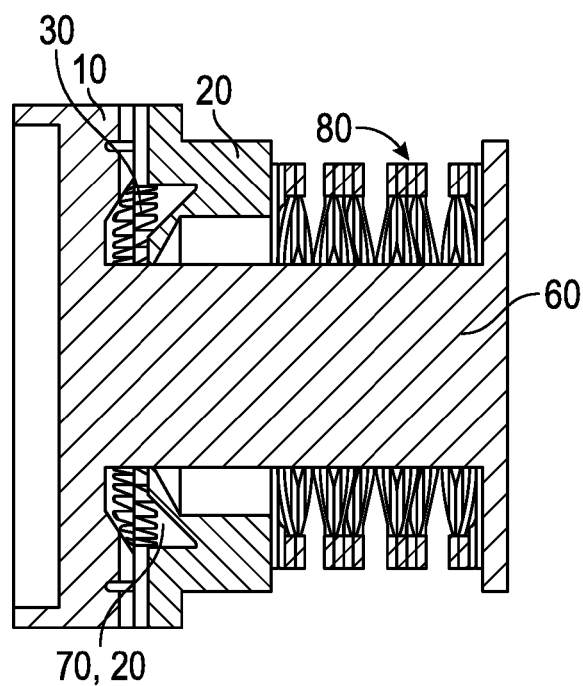
FIG. 6 is a side view of a ratchet mechanism in one embodiment of the invention.
Figure 7:
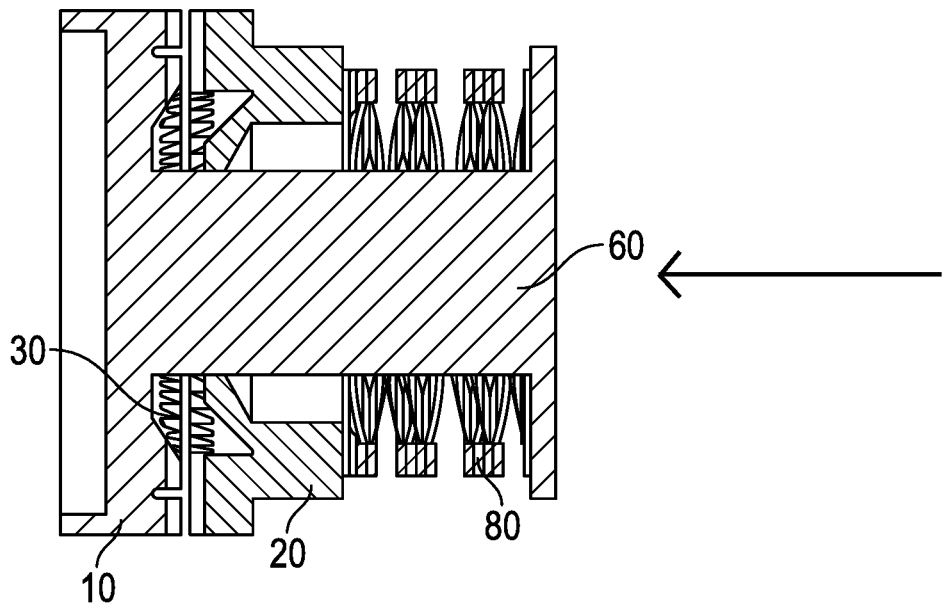
FIG. 7 is a side view of a ratchet mechanism in one embodiment of the invention.
Figure 8:
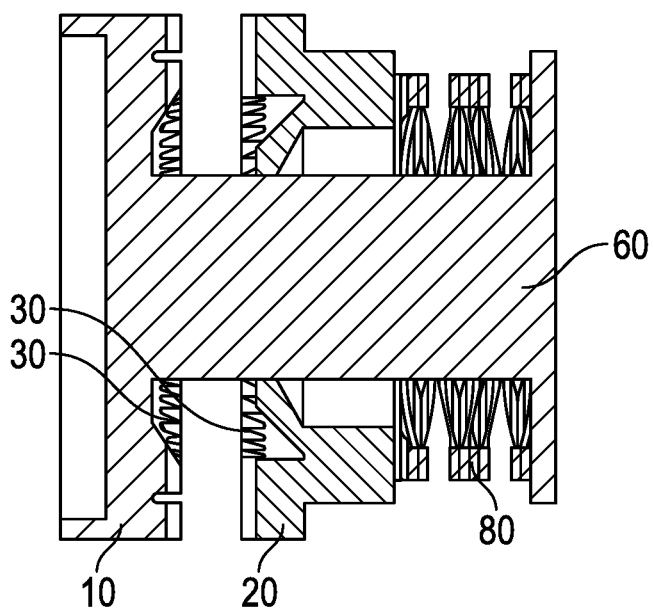
FIG. 8 is a side view of a ratchet mechanism in one embodiment of the invention in a single bypass initial configuration after application of external force A.
Figure 9:
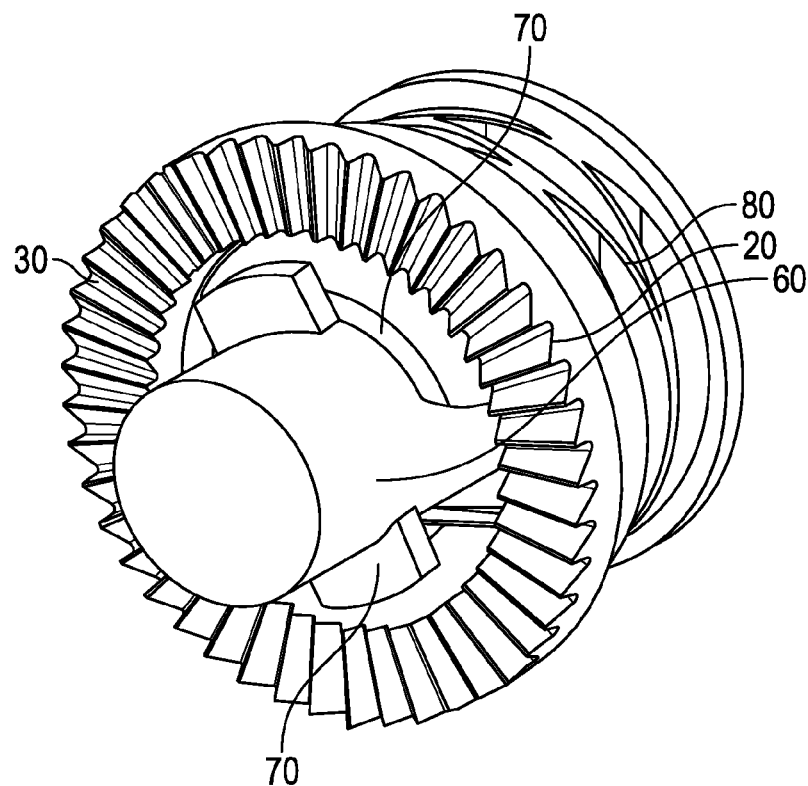
FIG. 9 is an isometric view of a ratchet mechanism in one embodiment of the invention in a single bypass initial configuration with disk 10 removed.
Figure 10:
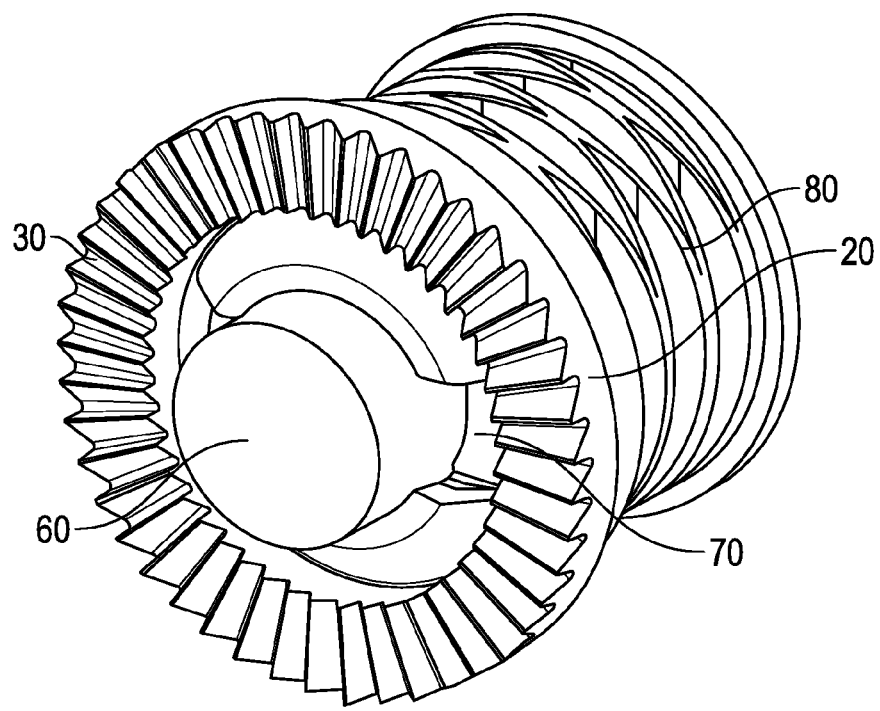
FIG. 10 is an isometric view of a ratchet mechanism in one embodiment of the invention in a single bypass final configuration with disk 10 removed.
Figure 11:
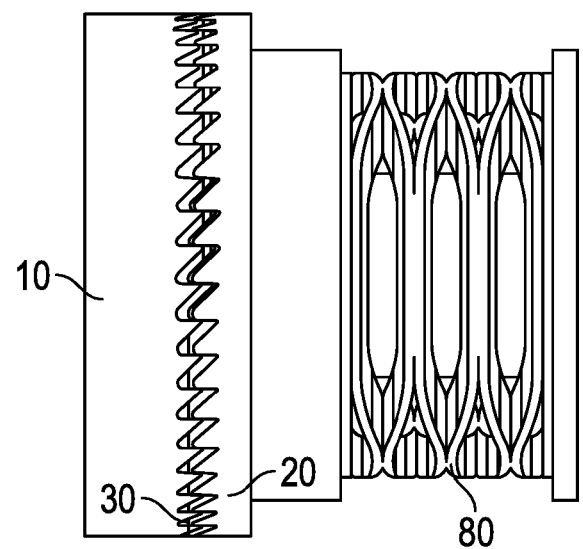
FIG. 11 is a side view of a ratchet mechanism in one embodiment of the invention in a single bypass final configuration.

With reference to FIGS. 6 and 7, the addition of a shaft (60) to one of the disks and a spring (80) to the mechanism provides a means to control the normal force between the two disks (10, 20) and bypass the mechanism when external force is provided.

The addition of cam features (70) to the disk without shaft (60) and to the shaft (60) on the opposing disk provides a means to bypass the mechanism (i.e., rotate the mechanism in the opposite direction) for a set angle of rotation one time (FIGS. 8, 9, 10 and 11). The cam features (70) on the shaft (60) shown in FIG. 9 rotate until they line up with cam features (70) on the other disk ( ) shown in FIG. 10. When aligned, the cam features (70) interlock, bringing the two disks (10, 20) together thereby engaging the teeth (30) ("arming" the device). The mechanism is then engaged and can rotate in only one direction. As such, incorporation of cam feature (70) allows the implementation of a one-time bypass operation of the double-row ratchet mechanism ("arming") that is set by two angular positions of the disks relative to each other.

The ratchet mechanism of the present invention may be utilized in any number of clamping type devices. In one embodiment, the ratchet mechanism is utilized in a wound claim device as described in U.S. patent application Ser. No. 14/103,641, the entire disclosure of which is incorporated herein by reference. In general terms, the wound closure device comprises needles which puncture the skin edges when the device is closed, and a pressure bar which applies pressure substantially perpendicular to the long axis of a wound. The present invention is embodied as end closure members which maintain the pressure bars in a closed position by a ratcheting mechanism.

Figure 12:
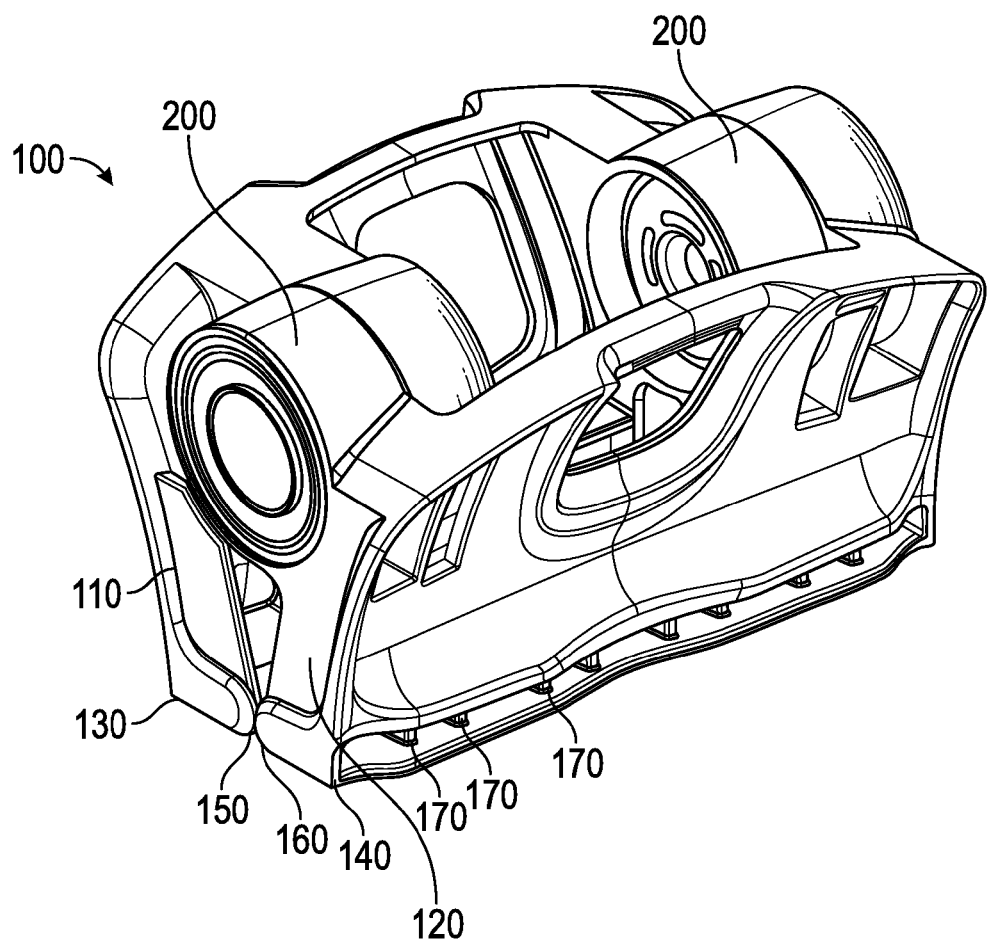
FIG. 12 is an isometric view of a wound clamp device having dual ratchet mechanisms in one embodiment of the invention.
Figure 13:
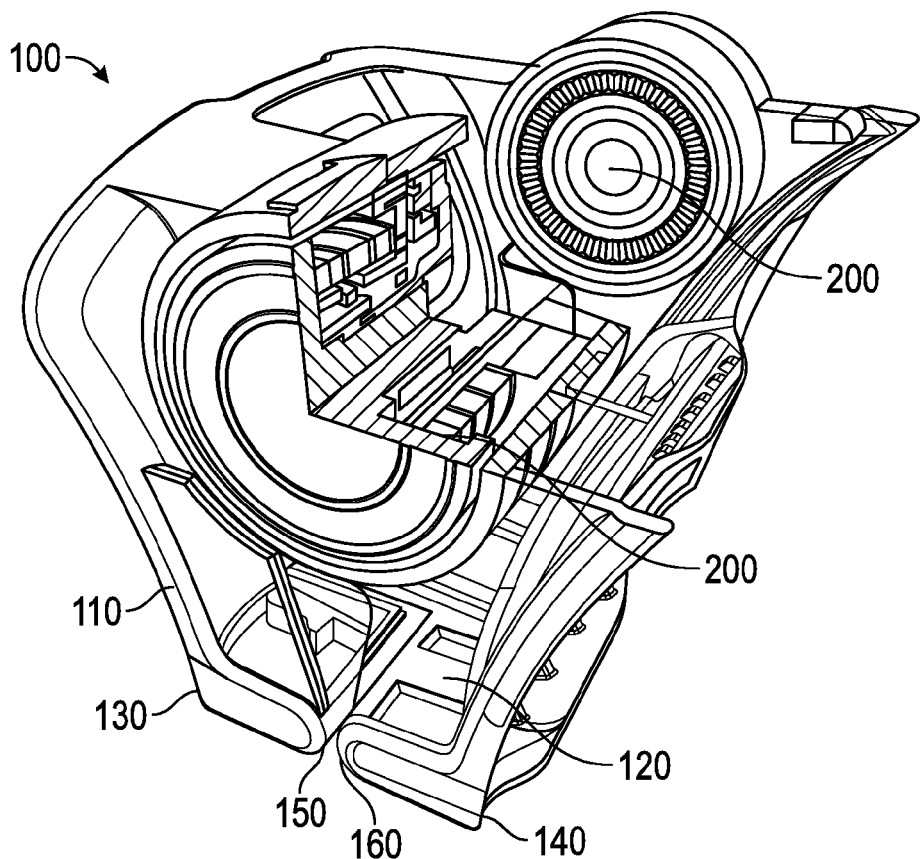
FIG. 13 is an isometric view of a wound clamp device having dual ratchet mechanisms in one embodiment of the invention with cut-away of one of the ratchet mechanisms.
Figure 14:
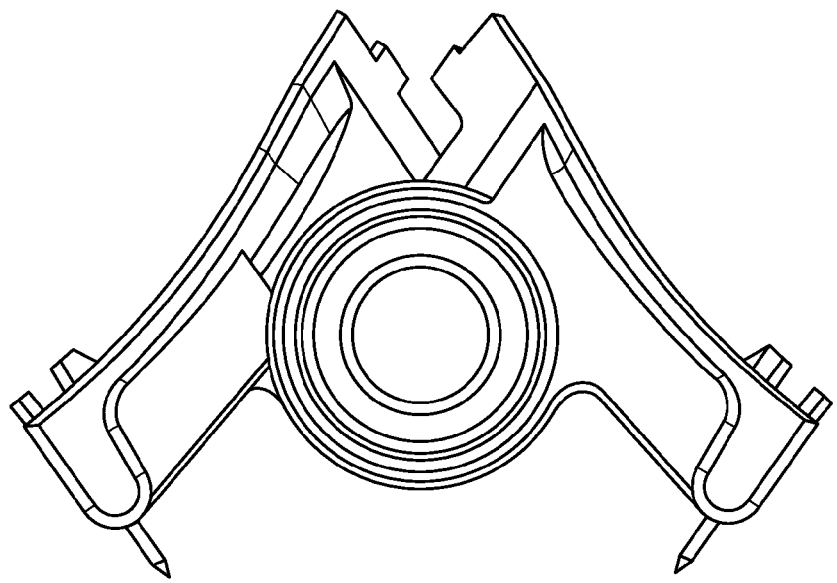
FIG. 14 is a front end view of the wound clamp device of FIGS. 12 and 13 in the open position in one embodiment of the invention.
Figure 15:
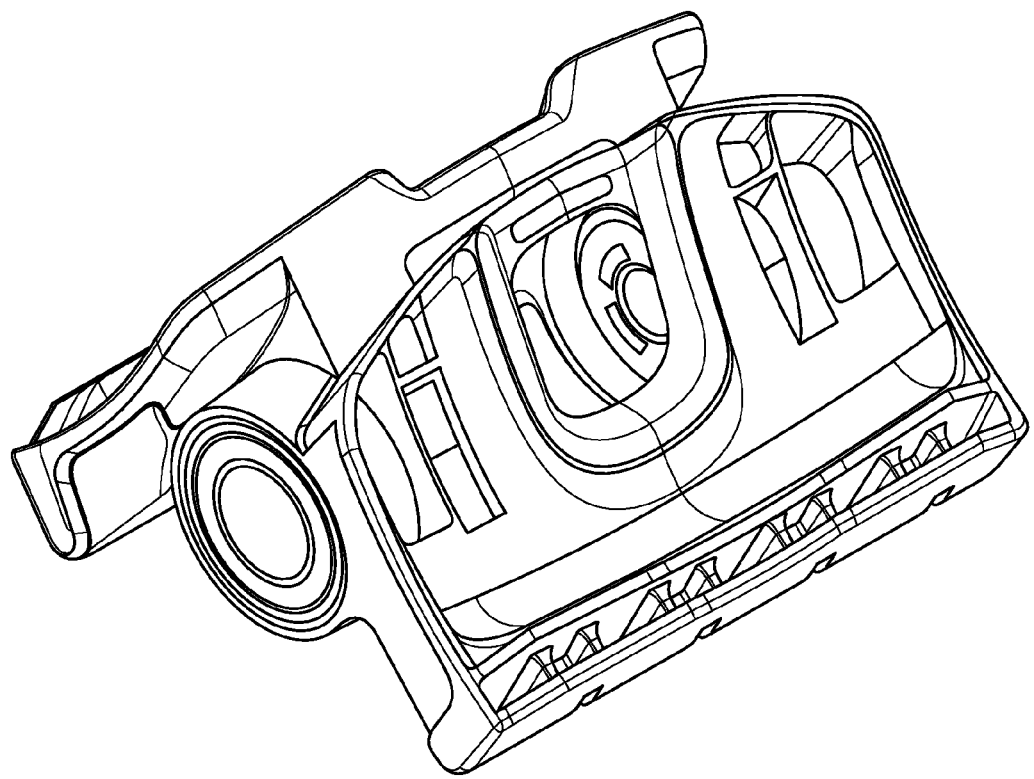
FIG. 15 is an isometric view of the wound clamp device of FIGS. 12 and 13 in the open position in one embodiment of the invention.
Figure 16:
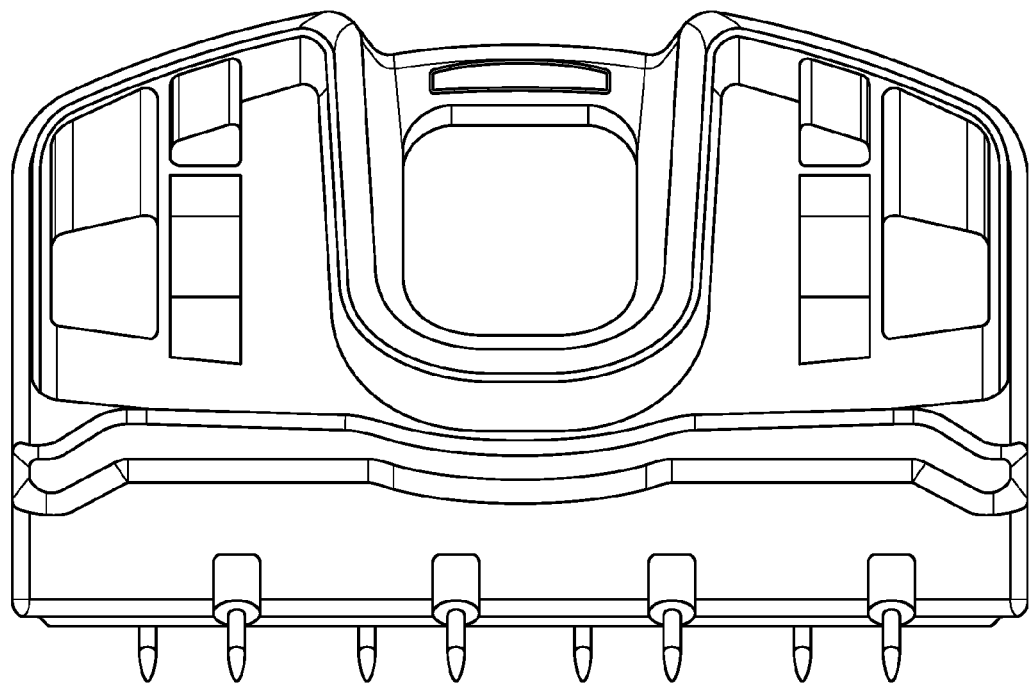
FIG. 16 is a side view of the wound clamp device of FIGS. 12 and 13 in the open position in one embodiment of the invention.
Figure 17:
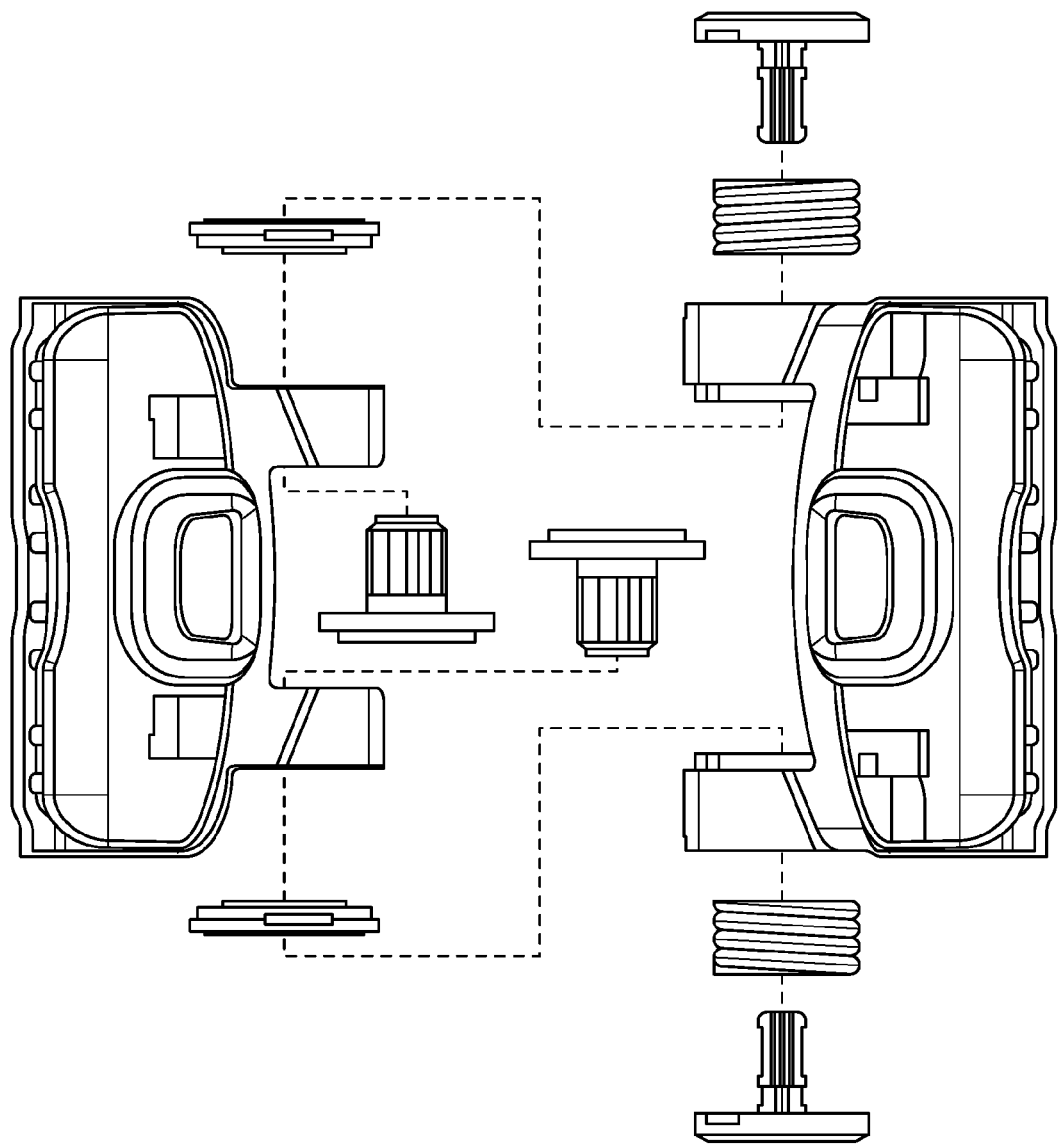
FIG. 17 is an expanded schematic of the wound clamp device of FIGS. 12 and 13 in the open position in one embodiment of the invention.
Figure 18:
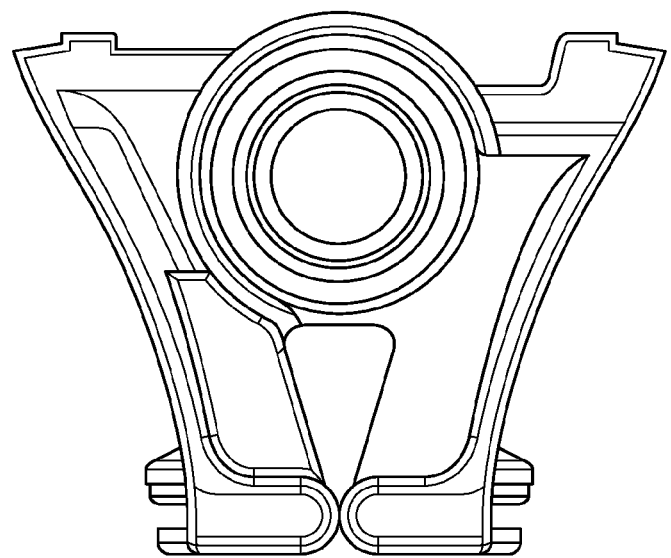
FIG. 18 is a front end view of the wound clamp device of FIGS. 12 and 13 in the closed position in one embodiment of the invention.
Figure 19:
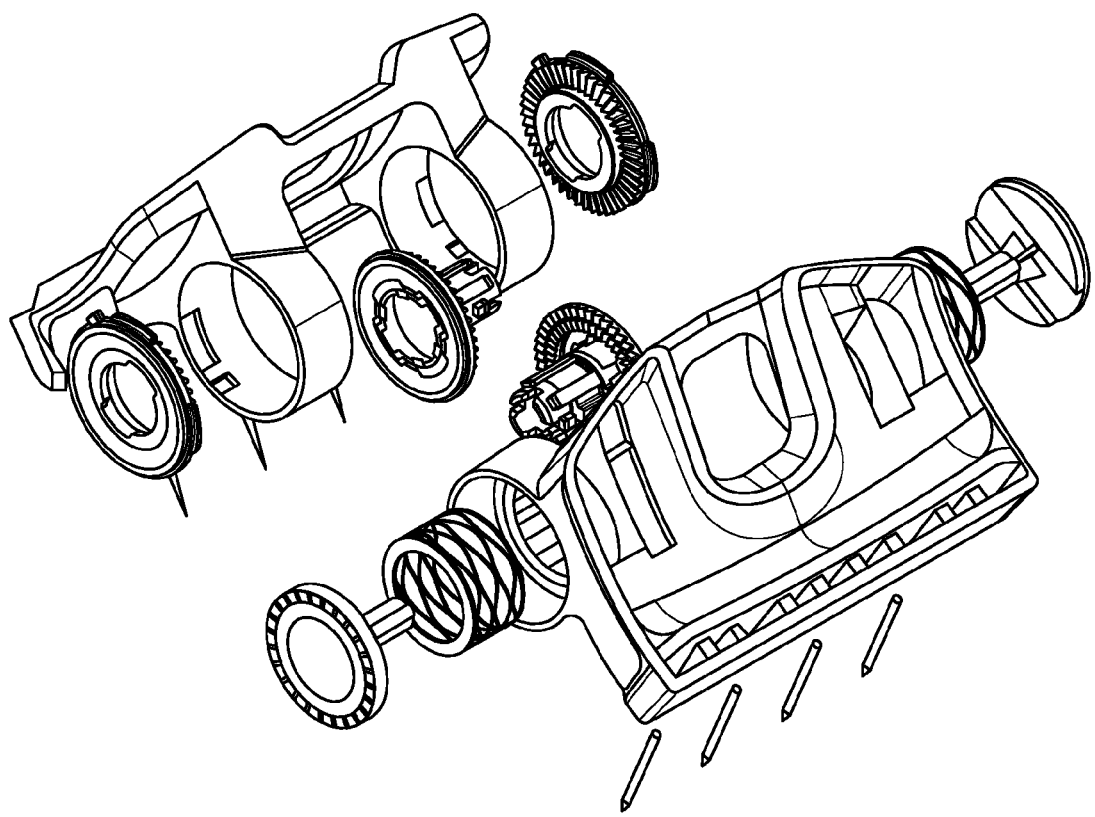
FIG. 19 is an expanded schematic of the wound clamp device of FIGS. 12 and 13 in the closed position in one embodiment of the invention.
Figure 20:
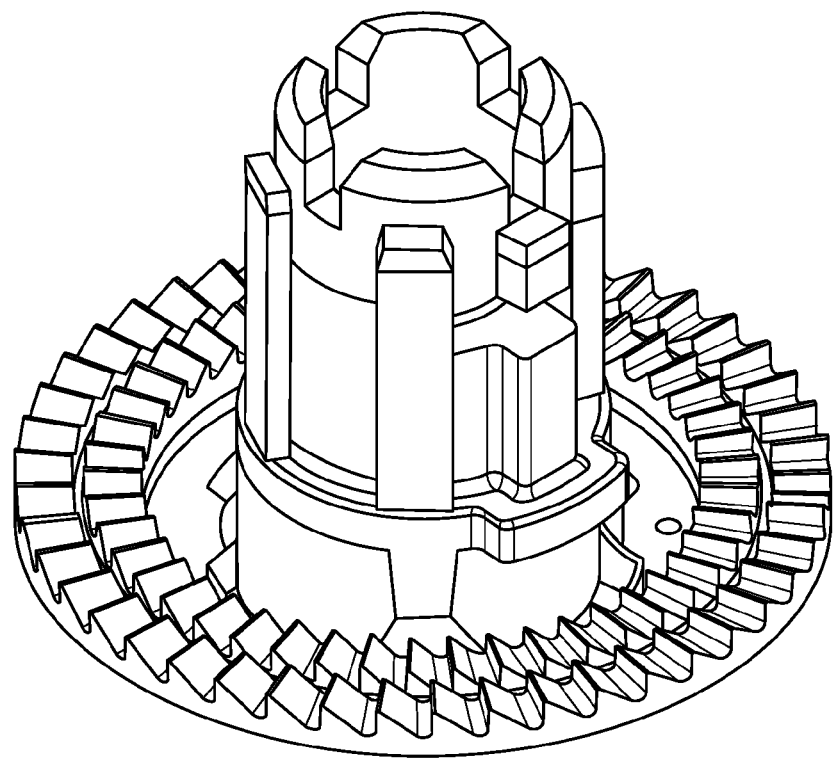
FIG. 20 is an isometric view of disc 10 of the wound clamp device of FIGS. 12 and 13 in one embodiment of the invention.
Figure 21:
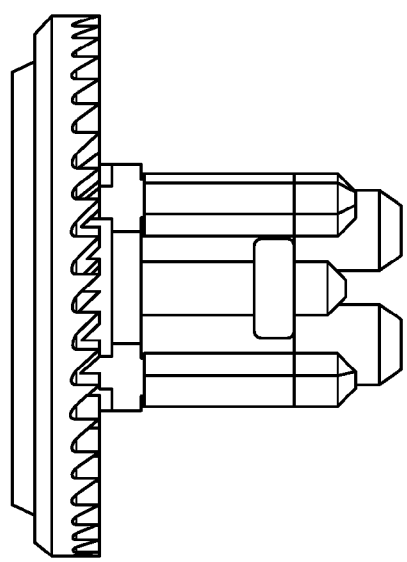
FIG. 21 is a side view of disc 10 of the wound clamp device of FIGS. 12 and 13 in one embodiment of the invention.
Figure 22:
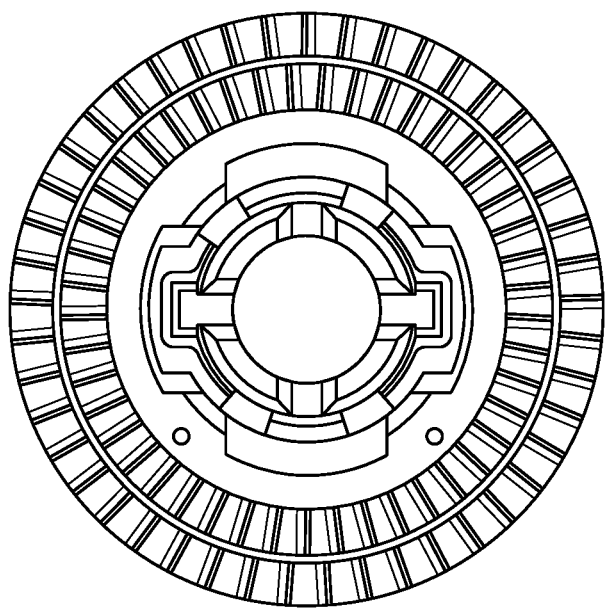
FIG. 22 is a front view of disc 10 of the wound clamp device of FIGS. 12 and 13 in one embodiment of the invention.
Figure 23:
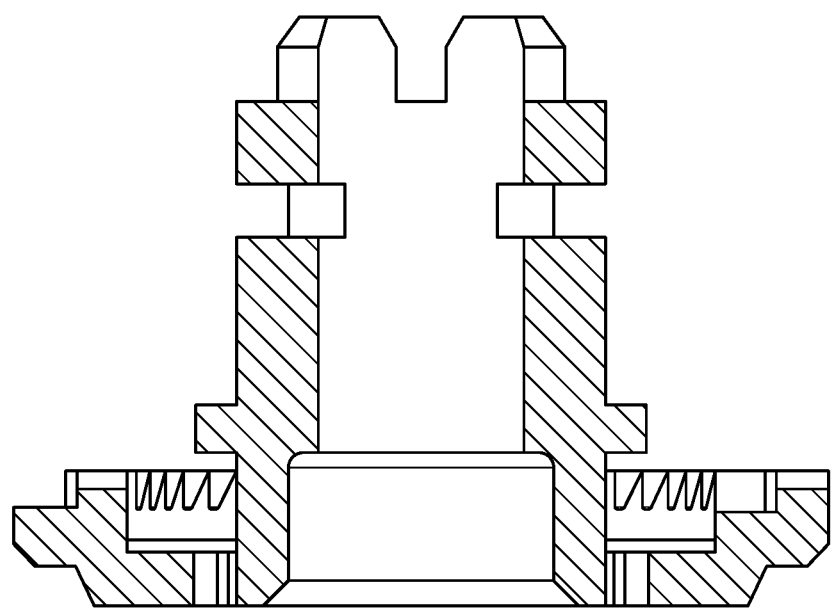
FIG. 23 is a cross-sectional view of disc 10 of the wound clamp device of FIGS. 12 and 13 in one embodiment of the invention.
Figure 24:
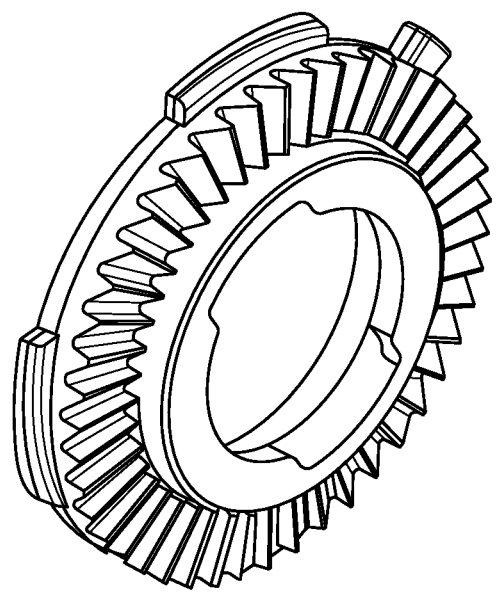
FIG. 24 is an isometric view of disc 20 of the wound clamp device of FIGS. 12 and 13 in one embodiment of the invention.
Figure 25:
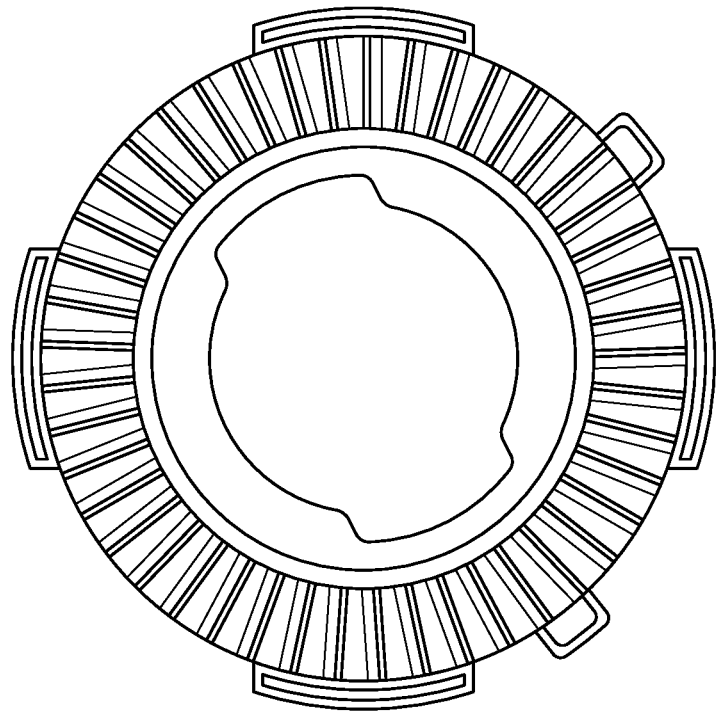
FIG. 25 is a front view of disc 20 of the wound clamp device of FIGS. 12 and 13 in one embodiment of the invention.

FIGS. 12 and 13 illustrate a wound clamp device of the present invention which incorporates a ratchet mechanism as described herein. The wound closure device (100) includes the ratchet mechanism of the present invention which includes: (a) a first opposing member (110) and a second opposing member (120) engaged about a longitudinal axis, each pivotally moveable around the axis between a closed position and an open position relative to each other, each of the opposing members having a proximal edge adjacent (130, 140) the longitudinal axis and a distal edge; (b) skin penetrating means for anchoring the device; (c) a pressure bar along each distal edge (150, 160); and (d) at least one ratchet mechanism (200) of the invention.

In general terms, one embodiment of the wound closure device is configured with a first opposing member (110) and a second opposing member (120) pivotally attached to each other about ratchet mechanisms (200) which defines a longitudinal axis of rotation. Each of the opposing members having an outer face and inner face and two ends. In one embodiment, each opposing member has a proximal edge (130, 140) and a distal edge (150, 160). The longitudinal pivoting axis is adjacent the proximal edge. When the first and second members are pivoted to an open position, the two distal edges are spread apart.

While the first and second opposing members (110, 120) are illustrated herein as having a particular geometry, they may be approximated by interconnected curved arms or another equivalent configuration.

Without restriction to a theory, the applicants believe that by closing the wound tightly, between the two opposing members and between the end closure members, blood loss from the wound can be minimized even if there are significant wounds below the surface of the skin, in a compressible zone of the body. The patient may then be transported to a surgical facility with a minimized risk of bleeding out in the meantime.

In one embodiment, the opposing members (110, 120) have needles (170) for piercing the skin on opposite sides of the wound. The needles have two primary functions. The first is to anchor the device into place when it is closed in place to seal a wound. If the device were to solely rely on frictional engagement with the skin, it might easily be knocked off. The second is to cause the skin and underlying tissue to bunch up between the opposing members. In one embodiment, the needles are long enough to penetrate the dermal layer (D) and extend into the underlying tissue. This action enhances the sealing action of the device.

In one embodiment, the needles (170) are alternately placed along the length of the opposing members such that the needles are interleaved. In one embodiment, the needles are curved such that the piercing of skin and closing of the device brings opposing edges of the wound up into the device. As a result, dermis to dermis contact along the length of the wound is promoted, which enhances the seal created by the device. As one skilled in the art will appreciate, the needles may have a radius of curvature similar to that of the first and second members.

In one embodiment, each of the opposing members (110, 120) has a pressure bar (150, 160) along the distal edge of each member. Once the device is closed on a wound, the pressure bars (150, 160) exert relatively even pressure along the length of the wound to close the wound. The pressure bar may comprise frictional elements to help grip the skin, such as ridges which run parallel to the distal edge.

In one embodiment, the pressure bar (150, 160) is configured to interact with or hide the needles of the opposing member in order to prevent exposing the needles when the device is being handled in the closed position. In one embodiment, the pressure bars may be lined with a resilient material which envelops the needle tips, such as neoprene or another rubbery material. The resilient material may also aid in the application of pressure to the wound.

In one embodiment, each of the opposing members (110, 120) has a grip on the outer face. In one embodiment, the grips are raised concave surfaces placed near the pivot axis.

In one embodiment, the device may be biased towards its open position by a first spring but is held in the closed position by cooperating ratchets (200) disposed on the first and second members. The ratchets (200) are disengaged by application of force along the longitudinal axis, as shown by the arrow in FIG. 7, allowing the device to be opened.

As discussed above, a plurality of engaging ratchet teeth permits the user to control the closed position. In the fully closed position, the distal edges of the opposing members are adjacent each other and the opposing needles overlap. A device in the open position may be closed on the wound by forcing the two opposing members closed, causing teeth of the ratchet mechanism to engage each other.

The scope of the invention includes alternative mechanical configurations which permit rotation of the two opposing members and a releasable locking or latching of the device into a closed position.

While the wound closure device shown in FIGS. 12 and 13 utilizes 2 ratchet mechanisms, it is envisioned that a device may utilize only one mechanism. Alternatively, a device may utilize 3, 4, 5, 6, 7, 8, 9 or more ratchet mechanisms. Additionally, the diameter of opposing disks utilized in the ratchet mechanisms may vary so long as the engaging members are disposed on the opposing discs in the manner described herein. As such, the size of the ratchet mechanism of the present invention is scalable for different applications.

In embodiments, multiple would closure devices may be applied to close a wound. For example, 2, 3, 4, 5, 6, 7 or greater wound closure devices may be applied to a wound. In one embodiment, the devices may be aligned side by side along the length of the wound.

In embodiments, the wound closure device may be configured with an accessory component adapted to directly or indirectly secure or anchor the device to another medical instrument. The wound closure device is anchored to the skin via pressure bars and skin penetrating means. The accessory component allows for rapid attachment of the accessory to the wound closure device, and takes advantage of the anchorage of the wound closure device into the skin to secure or anchor another medical instrument, such as a tube.

Attachment of accessory instruments to the wound closure device allows a variety of additional indications for use of the device. For example, an accessory port may be used as a means of inserting a device into a wound for delivery of therapeutics such as hemostatic agents, infection control agents, agents to reduce clot lysis and the like. Additionally, an accessory port may be used as a means inserting a device into a wound to remove material, such as a vacuum tube/dressing to create negative pressure through a suction device, or a needle decompression device to remove air from a chest wound.

In one embodiment, the wound closure device is provided as a kit comprising a wound closure device in a sterile package, which may be opened with one hand. Therefore, it may be seen that a user may take the sterile package, open it and remove the device which is stored in its closed position, open it with one hand, place it on a wound, and close it, all with one hand and in very little time.

The following examples are provided to further illustrate the advantages and features of the present invention, but are not intended to limit the scope of the invention. While they are typical of those that might be used, other procedures, methodologies, or techniques known to those skilled in the art may alternatively be used.

Example 1

Evaluation of Wound Closure Device with Ratchet Mechanism

A wound closure device was constructed having a ratchet mechanism of the present invention as shown in FIGS. 12 and 13. Several tests were performed using the device to evaluate various parameters regarding the functionality of the device utilizing ratchet mechanisms of the present invention. The various tests performed as well as test results are summarized in Table 1 below.

TABLE 1

Summary of Testing

| Test | Test Description | Acceptance Criteria | Sample Size | Recorded Data/Comments | Pass/Fail |
|---|---|---|---|---|---|
| Leakage Test | Functional Test to determine if the clamp can close and artificial wound and withstand water pressure of 180 mmHg (3.5 psi) for 30 s. This is to mimic a worse case scenario blood pressure. | Device must remain locked without any significant leakage at a water pressure of 180 mmHg maintained for 30 s. | 60 | Observations: All 60 Samples remained locked at a water pressure of 180 mmHg for 30 s. | Pass |
| Pressure Bar Relative Adjustment Force | This test evaluates the pressure bar relative adjustment increment (i.e. amount the pressure bars close for each increment/clog of the ratchet. | The maximum increment size without the pressure bars returning to their original position shall be less than 3 mm. | 10 | Min: 0.49 mm Max: 2.87 mm Average: 1.34 mm | Pass |
| Relaxation Backlash Test | This test procedure evaluates the clamp backlash after 24 hours holding a minimum load of 6.0 lbf-in. | The device shall not allow relative adjustment of the pressure bars of greater than 8 mm when a minimum holding torque of 6.0 lbf-in is applied for 24 hours. | 10 | Min: 0.87 mm Max: 2.53 mm Average: 1.69 mm All 10 samples allowed less than 8 mm of backlash. | Pass |
| Maximum Arming Force | This test procedure determines the force required to open (arm) the device (i.e. arm the ratchet. | The force required to arm the device shall be less than 6.3 lbf. | 60 | The maximum arming force observed was 3.20 lbf. All 60 samples required less than 6.3 lbf to arm the device. | Pass |
| Maximum Closing Force | This test procedure determines the force required to close the device (i.e. close the ratchet. | The force required to close the device shall be less than 7.9 lbf. | 60 | The maximum closing force observed was 2.55 lbf. All 60 samples required less than 7.9 lbf to close the device. | Pass |
| Minimum Holding Torque | Using a tensile tester, this test procedure tests the ability of the clamp to hold a minimum torque of 8.0 lbf-in. | The device one-way locking mechanism must maintain a minimum holding torque of 8.0 lbf-in. | 60 | Observations: All of the 60 were able to hold a minimum torque of 8.0 lbf-in. | Pass |
| Backlash Test | Using a tensile tester, this test procedure tests the backlash of the clamp at a minimum torque of 8.0 lbf-in. | The one-way locking mechanism will allow less than 4 mm of backlash at a minimum holding torque of 8.0 lbf-in. | 10 | Min: 0.87 mm Max: 3.79 mm Average: 1.59 mm All 10 samples allowed less than 4 mm of backlash. | Pass |

What is claimed is:

1. A ratchet mechanism comprising:
   (a) a first opposing disk and second opposing disk rotationally engagable about a longitudinal axis and being rotationally movable about the axis between an open position and a closed position, each disk having a plurality of engaging members disposed on opposing surfaces of each disk such that movement of the mechanism from the open position to the closed position causes opposing rotational movement of each disk relative to one another, wherein the plurality of engaging members maintains the opposing disks in the closed position upon movement of the ratchet from the open position to the closed position,
   wherein the plurality of engaging members are arranged as teeth radially disposed around each opposing surface, and wherein the engaging members of one of the first or second disks are arranged as concentric outer and inner circles, each circle being radially offset to the other;
   (b) a shaft having a first end and a second end, the shaft extending from the second disk along the longitudinal axis toward the first disk from the first end to the second end;
   (c) a resilient member arranged along the longitudinal axis between the first disk and the second end of the shaft, wherein application of force to the first end of the shaft along the longitudinal axis disengages the plurality of engaging members allowing opposing rotational movement of the disks from the closed position to the open position.

2. The ratchet mechanism of claim 1, wherein the engaging members of the first disk are arranged as a single circle and the engaging members of the second disk are arranged as concentric circles.

3. The ratchet mechanism of claim 1, wherein the engaging members of the second disk are arranged as a single circle and the engaging members of the first disk are arranged as concentric circles.

4. The ratchet mechanism of claim 1, wherein the inner and outer circles of engaging members are radially offset by half the angular distance of that between engaging members.

5. The ratchet mechanism of claim 1, wherein the resilient means is a spring disposed along the longitudinal axis.

6. The ratchet mechanism of claim 1, wherein the inner and outer circles each comprise the same number of teeth.

7. The ratchet mechanism of claim 1, wherein the inner and outer circles each comprise a different number of teeth.

8. The ratchet mechanism of claim 1, wherein the first disk, inner circle and outer circle each have the same number of engaging members.

9. The ratchet mechanism of claim 1, wherein the first and second disk have the same diameter.

10. The ratchet mechanism of claim 1, wherein the mechanism is biocompatible.

11. The ratchet mechanism of claim 1, wherein the shaft comprises one or more cams which interlock with the first or second disks upon movement from the open to closed position.

12. The ratchet mechanism of claim 1, wherein the first, second or both opposing disks are coated with a friction altering agent.

13. A wound closure device comprising:
    (a) a first opposing member and a second opposing member engaged about a longitudinal axis, each pivotally moveable around the axis between a closed position and an open position relative to each other, each of the opposing members having a proximal edge adjacent the longitudinal axis and a distal edge, and an outer face and an inner face;
    (b) the ratchet mechanism of claim 1, wherein the first disk is on the first member, and the second disk is on the second member; and
    (c) a plurality of needles disposed on the distal edges of the first and second members.

14. The wound closure device of claim 13, further comprising a pressure bar attached to the distal end of each of the opposing members.

15. The wound closure device of claim 14, further comprising a stabilizer bar attached to the outer face of each opposing member.

16. The wound closure device of claim 13, further comprising a grip attached to the outer face of each opposing member, wherein the grip comprises a first gripping surface parallel to the longitudinal axis, and a gripping surface substantially perpendicular to the first gripping surface.

17. The wound closure device of claim 13, wherein each opposing member is semi-cylindrical.

18. The wound closure device of claim 13, wherein the needles are straight or are curved, with a radius of curvature substantially similar to the radius of curvature of the opposing members.

19. The wound closure device of claim 13, further comprising one or more additional ratchet mechanisms.

20. The wound closure device of claim 13, further comprising a medical instrument coupled to the accessory component.

21. The wound closure device of claim 20, wherein the medical instrument is selected from a needle, tube, catheter, and cannula.

22. The wound closure device of claim 13, further comprising an integrated port.

23. The wound closure device of claim 13, further comprising an accessory component.

24. The wound closure device of claim 23, wherein the accessory component comprises means for securing a medical device to the wound closure device.

25. The wound closure device of claim 24, wherein the accessory component comprises an articulated arm.

26. A wound closure device comprising:
    (a) a first opposing member and a second opposing member engaged about a longitudinal axis, each pivotally moveable around the axis between a closed position and an open position relative to each other, each of the opposing members having a proximal edge adjacent the longitudinal axis and a distal edge;
    (b) skin penetrating means for anchoring the device;
    (c) a pressure bar along each distal edge; and
    (d) a ratchet mechanism of claim 1.

27. The device of claim 26, wherein each opposing member comprises an end closure member substantially perpendicular to the distal edge and aligned with an opposing end closure member.

28. The device of claim 26, wherein the skin penetrating means comprises a plurality of needles disposed along each pressure bar.

29. The device of claim 28, wherein the needles are of sufficient length to penetrate the skin and pierce underlying tissue.

30. The device of claim 28, wherein the needles are straight or are curved, with a radius of curvature substantially similar to a radius of curvature of the opposing members.

31. The device of claim 26, wherein the device comprises at least two ratchet mechanisms.

32. The device of claim 26, further comprising an accessory component.

33. The wound closure device of claim 32, wherein the accessory component comprises means for securing a medical device to the wound closure device.

34. The wound closure device of claim 33, wherein the accessory component comprises an articulated arm.

35. The wound closure device of claim 26, further comprising a medical instrument coupled to the accessory component.

36. The wound closure device of claim 35, wherein the medical instrument is selected from a needle, tube, catheter, and cannula.

37. The wound closure device of claim 26, further comprising an integrated port.

38. A method for performing a medical procedure on a subject, comprising:
 (a) deploying the wound closure device of any of claims 13 or 26 to a wound of the subject; and
 (b) actuating the wound clamp device to effectuate approximation of skin tissue and closing of the wound closure device.

39. The method of claim 38, further comprising coupling a medical instrument to the wound closure device.

40. The wound closure device of claim 39, wherein closing of a wound skin is lifted and approximated between the pressure bars.

* * * * *